United States Patent [19]

Shelleman et al.

[11] Patent Number: 5,220,824
[45] Date of Patent: Jun. 22, 1993

[54] HIGH TEMPERATURE, TUBE BURST TEST APPARATUS

[75] Inventors: David L. Shelleman, State College, Pa.; Darryl P. Butt, Los Alamos, N. Mex.; John R. Hellmann, State College; Richard E. Tressler, Boalsburg, both of Pa.; John J. Mecholsky, Jr., Gainesville, Fla.

[73] Assignee: The Pennsylvania Research Corporation, University Park, Pa.

[21] Appl. No.: 748,174

[22] Filed: Aug. 20, 1991

[51] Int. Cl.⁵ .................................. G01M 3/00
[52] U.S. Cl. ........................ 73/49.5; 73/49.8; 374/57
[58] Field of Search ............. 73/49.1, 49.5, 37, 865.6, 73/49.8; 374/57

[56] References Cited

U.S. PATENT DOCUMENTS

| | | | |
|---|---|---|---|
| 2,592,984 | 4/1952 | Walling | 73/37 |
| 2,685,060 | 7/1954 | Pierce et al. | 324/15 |
| 2,966,791 | 1/1961 | Ivins | 73/12 |
| 3,365,933 | 1/1968 | Jorgensen et al. | 73/37 |
| 3,557,606 | 1/1971 | Markey | 73/37.8 |
| 3,785,195 | 1/1974 | Yasuhiro et al. | 73/37 |
| 3,916,673 | 11/1975 | Gass et al. | 73/37 |
| 3,955,402 | 5/1976 | Harvill | 73/37 |
| 3,958,448 | 5/1976 | Willis et al. | 73/37 |
| 4,081,990 | 4/1978 | Chatagnier | 73/49.1 |
| 4,385,643 | 5/1983 | Noe | 73/49.1 |
| 4,548,069 | 10/1985 | Nonsak | 73/49.1 |
| 4,553,425 | 11/1985 | Tkachuk | 73/37 |
| 4,763,529 | 8/1988 | Leonard et al. | 73/865.6 |
| 4,788,850 | 12/1988 | Buschor et al. | 73/49.2 |
| 4,990,312 | 2/1991 | Rucker et al. | 73/865.6 |

Primary Examiner—Tom Noland
Assistant Examiner—Michael Brock
Attorney, Agent, or Firm—Perman & Green

[57] ABSTRACT

A testing apparatus is described that enables both single and double-ended tubular members to be tested under pressure and at elevated temperatures. For double-ended tubular members, the apparatus comprises first and second pressure seals at either end of the tubular member under test, both seals including annular compliant members that bear upon the internal surface of the tubular member. A heater is positioned within the tubular member and one of the pressure seals has an orifice through which the heater is connected to a power source. Pressurization occurs through an orifice in the other pressure seal and cooling apparatus surrounds the first and second ends of the tubular member to cool the pressure seals, thereby enabling the annular compliant members to retain their compliancy when the tubular member is heated to test temperature. For single-ended tubular members, a single pressure seal is used having pathways for both electrical and pressurization connections to the interior of the tubular member.

11 Claims, 3 Drawing Sheets

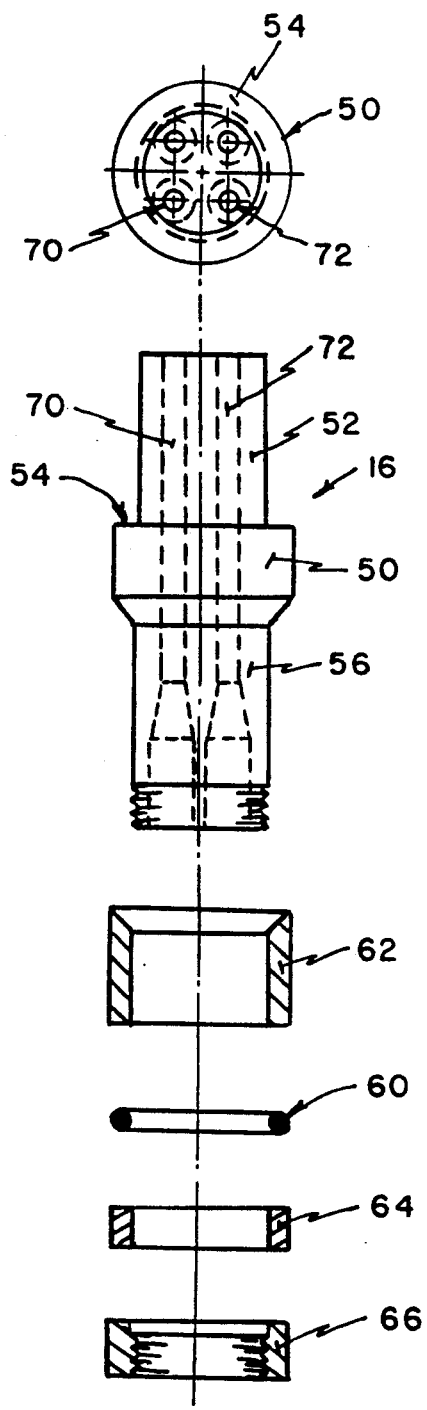
FIG. 3
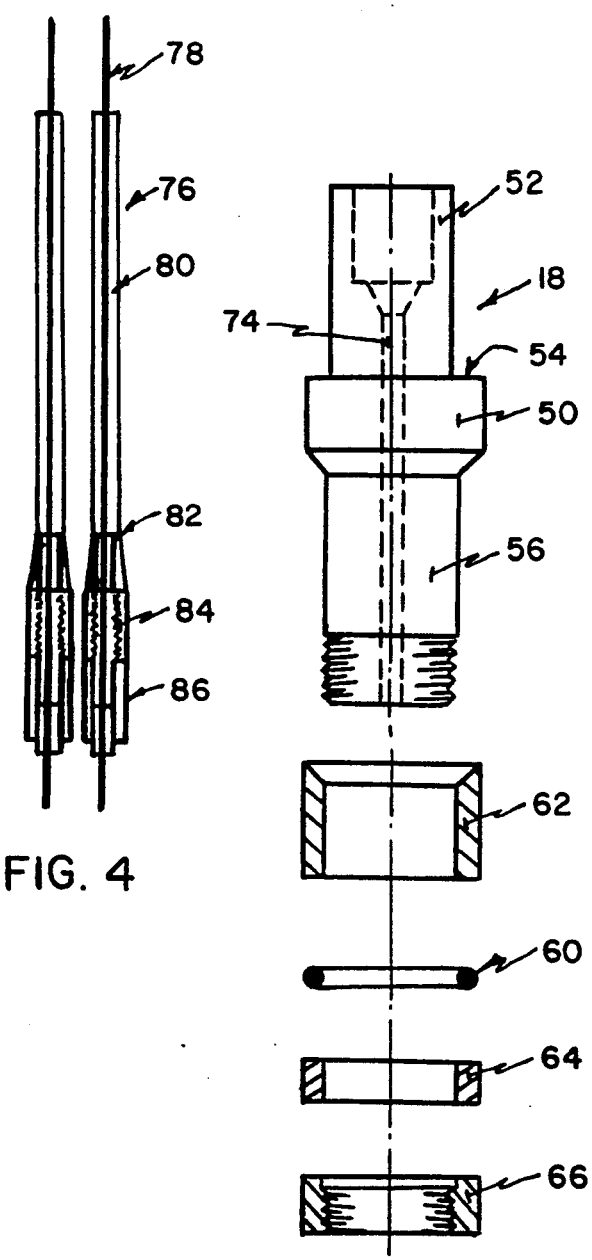
FIG. 4
FIG. 5

HIGH TEMPERATURE, TUBE BURST TEST APPARATUS

FIELD OF THE INVENTION

This invention relates to testing apparatus, and more particularly, to testing apparatus particularly designed to test ceramic tubular members at high temperature and under high pressure.

BACKGROUND OF THE INVENTION

In order to design reliable ceramic components, it is essential to be able to predict their behavior under in-service conditions. Typically, small scale laboratory strength studies are performed on ceramic specimens under a known stress state, i.e., flexure and/or tension. The studies are performed at room temperature to establish base line strength data from which to assess the effects of other variables (e.g., temperature and environment) on the strength behavior of the ceramic material. Industrial components are often subjected in actual use to complex stress states which are unable to be simulated in the laboratory.

Size also affects the strength characteristics of ceramics, in that, with increased size, the strength of ceramic components generally decreases. This affect is attributable to the nature and distribution of intrinsic microscopic flaws that are unavoidably present as a result of material processing and/or handling. Similarly, for materials which exhibit creep or time dependent strength behavior at elevated temperatures, laboratory studies can be performed on small specimens to predict the lifetime of a component. Statistics from such studies predict the strength and reliability of the ceramic component under test. However, the inability to test full size components in service environments causes such statistics to be subject to question.

Ceramic tubes are widely used in radiant tube and heat exchanger applications. It is desirable to clarify the failure possibility of such tubes under actual operating (temperature and pressure) conditions.

Pressure testing of ceramic components is known in the prior art. Much of that prior art relates to pressure testing of glass and other ceramic types of bottles. In U.S. Pat. No. 3,785,195 to Yasuhiro (see FIGS. 5 and 6), an annular packing is caused to expand and seal the interior of a bottle's throat so that a pressure test can be accomplished. The sealing action occurs due to an upwards movement of a nozzle portion of the sealing mechanism with respect to a collar, thereby causing expansion of the annular packing. In U.S. Pat. No. 2,592,984 to Walling, another bottle pressure testing system is shown wherein (see FIG. 5) the neck of the bottle is forced against a resilient member sealer while pressure testing occurs.

Additional bottle testing systems can be found in U.S. Pat. Nos. 3,958,448 to Willis et al., 3,955,402 to Harvill, and 4,788,850 to Buschor.

Other testing systems for pressure testing vessels can be found in U.S. Pat. Nos. 3,365,933 to Jorgensen et al., 4,553,424 to Tkachuk and 3,916,673 to Gass et al. Pressure testing has also been applied to systems, e.g., see 2,685,060 to Pierce et al. (spark plugs); 2,966,791 to Ivans (explosive testing) and 3,557,606 to Markey (for gauging work piece dimensions as a work piece undergoes fluid pressure expansion). None of the above cited prior art indicates an ability to test a ceramic vessel at elevated temperature while maintaining a high pressure sealing action at vessel openings.

Accordingly, it is an object of this invention to provide an improved high pressure, high temperature test apparatus for tubular members.

It is another object of this invention to provide an improved high temperature, high pressure testing apparatus wherein pressure seals maintain their sealing action under the high temperature conditions.

It is a further object of this invention to provide a high temperature, high pressure testing apparatus for ceramic tubes wherein such tubes can be tested to failure under conditions of safety.

SUMMARY OF THE INVENTION

A testing apparatus is described that enables a tubular member to be tested under pressure and at elevated temperature. The apparatus comprises first and second pressure seals at either end of the tubular member under test, both seals including annular compliant members that bear upon the internal surface of the tubular member. A heater is positioned within the tubular member and one of the pressure seals has an orifice through which the heater is connected to a power source. Pressurization occurs through an orifice in the other pressure seal, and cooling apparatus surrounds the first and second ends of the tubular member to cool the pressure seals, thereby enabling the annular compliant members to retain their compliancy when the tubular member is heated to test temperature.

DESCRIPTION OF THE DRAWINGS

FIG. 3 is an exploded view of a first pressure seal.

FIG. 4 is a plan view of a pair of electrical feedthroughs.

FIG. 5 is an exploded view of a second pressure seal.

FIG. 6 is a partial sectional view of a single-ended tube under test.

DETAILED DESCRIPTION OF THE INVENTION

Test apparatus incorporating the invention hereof is preferably capable of operating at temperatures up to 1400° C., testing tube sizes up to 8 inches in diameter, enabling internal gas pressurizations up to 10 Ksi, and retaining for analyses tube fragments at the conclusion of the test.

Figure 1:
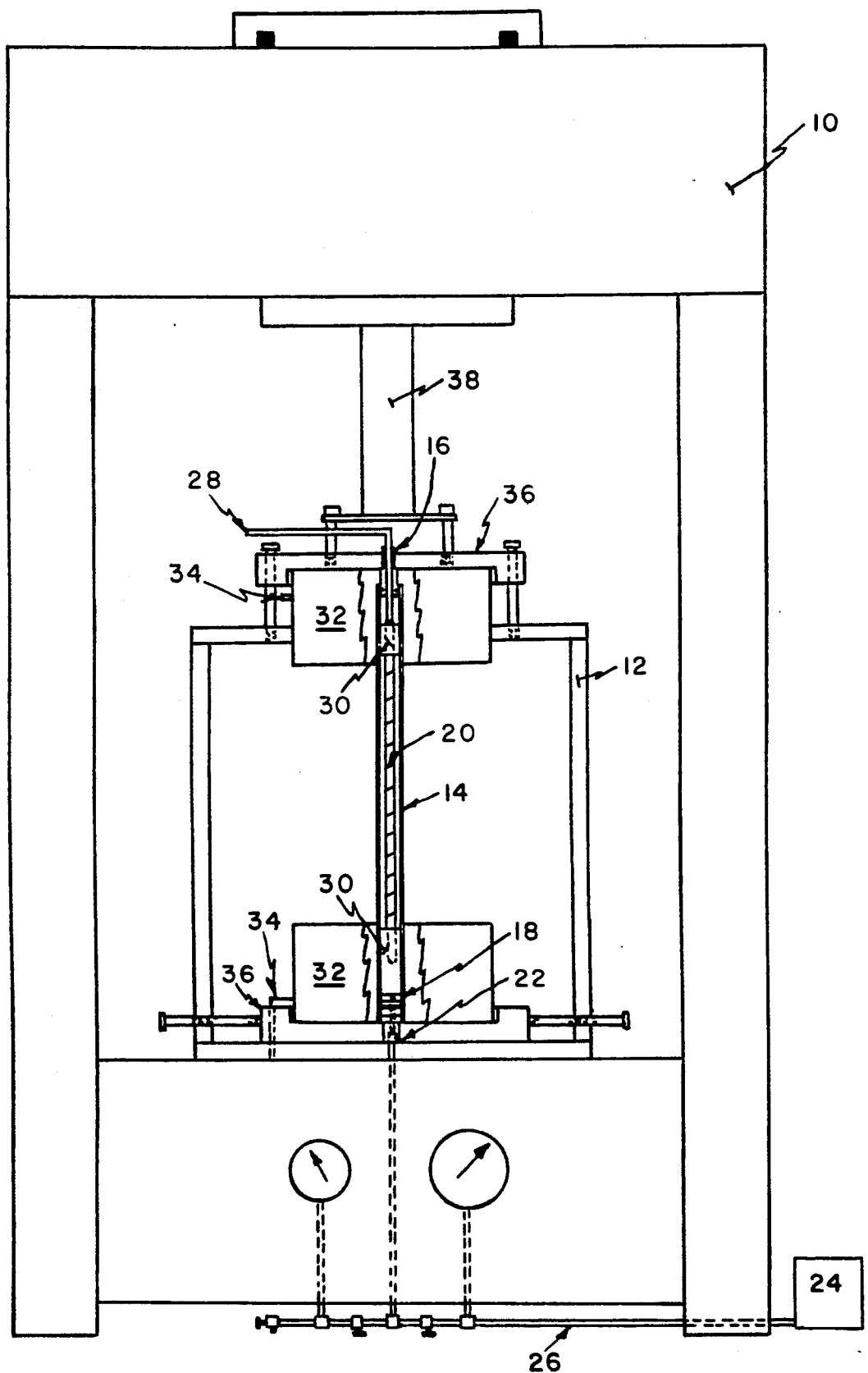
FIG. 1 is a plan view of the test system that incorporates the invention.
Figure 2:
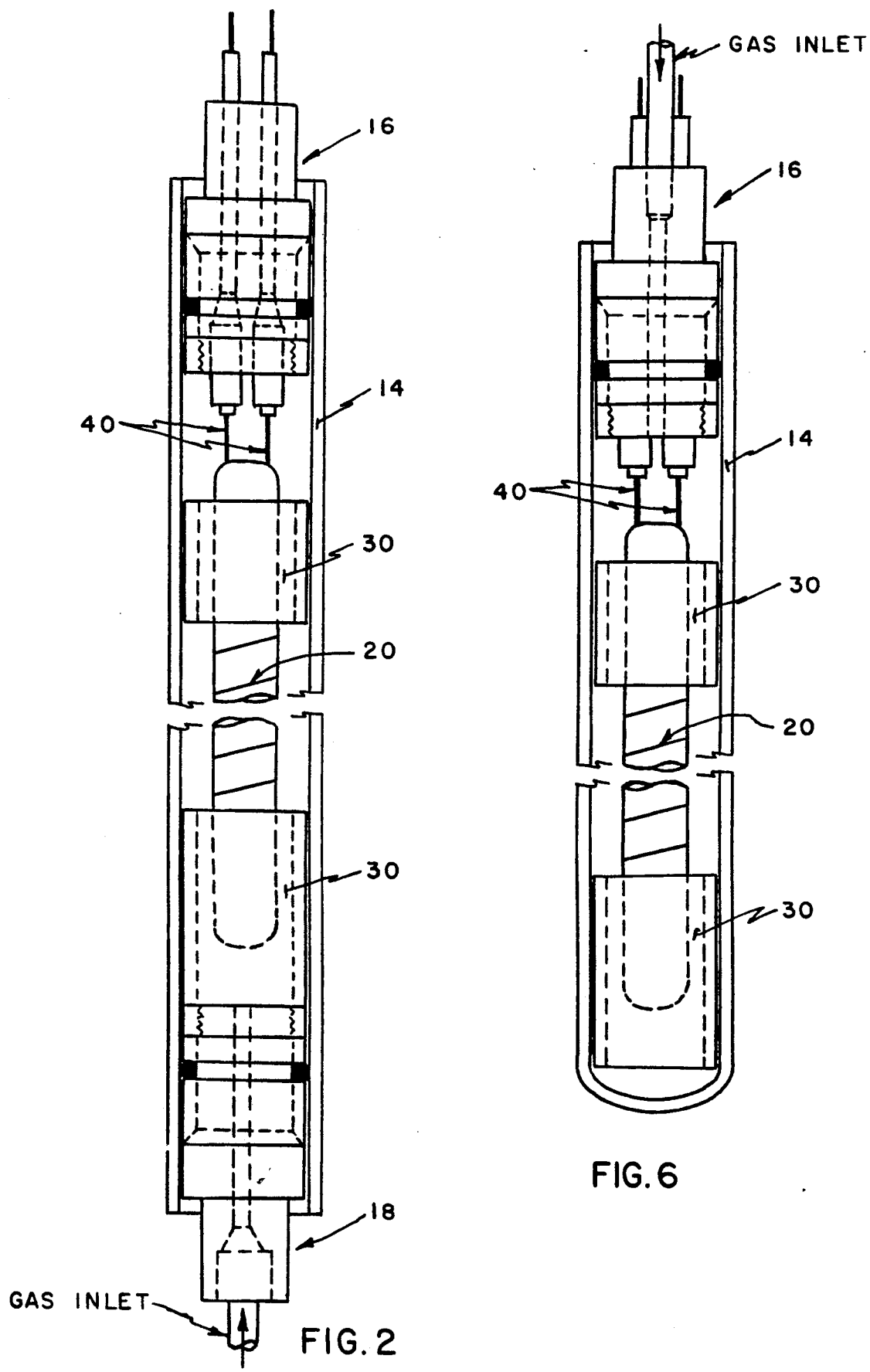
FIG. 2 is a partial sectional view of a tube under test showing the high pressure seals and heating element.

Referring to FIG. 1, the test apparatus is contained within a frame press 10 which maintains system integrity when a tube under test is pressurized. An explosion-resistant, steel test chamber 12 encompasses the test area and includes a fiber filler (not shown) to capture fragments of the tube under test after it has fractured. The tube under test is indicated at 14 and floats freely on internal O-rings integral to pressure seals 16 and 18. The details of this structure are shown in FIG. 2 and will be described in detail below.

Heating is achieved by an electrical resistance, bayonet-style silicon carbide heating element 20 which extends into the interior of tube 14. Gas pressurization of tube 14 is accomplished via an orifice 22 within lower pressure seal 18, using conventional gas boosting equipment. A source of pressurized gas 24 provides a gas feed via piping 26 and orifice 22 into the interior of tube 14.

Heating element 20 is connected to electrical vias (feed-throughs) that extend through upper pressure seal 16 and, in turn, is connected through conductors 28 to a source of power. A pair of boron nitride inserts 30 surround heating element 20 and prevent it from contacting the internal surface of tube 14.

Aluminum blocks 32 surround both the upper and lower regions of tube 14 and pressure seals 16 and 18. Each of aluminum blocks 32 is water cooled via tubes 34 to maintain pressure seals 16 and 18 at a cool temperature. This assures that the O-rings in pressure seals 16 and 18 maintain their flexibility when heating element 20 is energized.

Cooling blocks 32 are maintained in position by base plates 36 which are, in turn, biased towards each other by post 38 that extends down from the upper-most portion of frame press 10. Thus, when tube 14 is pressurized, expanded shoulders of pressure seals 16 and 18 bear upon plates 36. However, press 10 maintains plates 36 (and seals 16 and 18) in place and preserves the functional integrity of the test system.

Turning now to FIGS. 2-5, the details of pressure seals 16, 18 and the internal aspects of tube 14 will be hereafter described. In FIG. 2, tube 14 is shown in section whereas pressure seals 16 and 18 are shown in full.

Electrical-resistance, bayonet-style silicon carbide heating element 20 internally heats ceramic tube specimen 14. Power leads 40 are fastened to the upper end of heating element 20 and are preferably insulated from the heating element by a ceramic fiber fabric (not shown). Also surrounding the upper portion of heating element 20 is a boron nitride cylinder 30 which serves as a thermal barrier for upper pressure seal 16 and prevents heating element 20 from contacting the internal surface of tube 14. A lower boron nitride cylinder 30 performs a similar function for lower pressure seal 18.

Both ends of tube 14 are sealed by internal pressure seals 16 and 18. FIGS. 3 and 5 show the details of pressure seals 16 and 18, respectively, and FIG. 4 shows conductor feedthroughs which mate with passageways in pressure seal 16. As shown in FIGS. 3 and 5, each of pressure seals 16 and 18 comprises a cold-rolled steel shaft which has been machined to include expanded collars 50. The upper portions of each of pressure seals 16 and 18 are machined to mate with orifices in end plates 36. When assembled, shoulders 54 of collars 50 bear upon the adjacent surfaces of end plates 36.

The lower portions 56 of each of pressure seal 16 and 18 are machined to accommodate the inner diameter of a fluorocarbon O-ring 60 and a pair of bushings 62 and 64. The lower-most end of portion 56 is threaded and accommodates a threaded collar 66.

O-ring 60 acts as a compression seal when placed between bushings 62 and 64. These bushings are machined to have an outer diameter that is in the range of 0.004–0.008 inches undersize relative to the inner diameter of tube 14. In essence, the outer diameter of bushings 62 and 64 exhibit a slip-fit relationship with the inner diameter of tube 14.

When assembled, each of pressure seals 16 and 18 is inserted so that its lower portion 56 resides in the interior of tube 14. Prior to insertion, threaded collar 66 is tightened to provide an initial compression of O-ring 60. This insures an initial snug fit between O-ring 60 and the inner wall of tube 14 and prevents gas leakage during initial pressurization. During pressurization, bushing 64 is forced towards collar portion 50, thereby compressing O-ring 60 and, additionally, forcing bushing 62 against collar 50. As the pressure continues to build inside tube 14, O-ring 60 produces a tighter seal, and at the same time, supports tube 14 equally around its inner periphery. Thus, at the same time a gas-tight pressure seal is created, tube 14 is supported in such a manner that unequal stresses therein are avoided.

Pressure seal 16 is provided with internal passageways 70 and 72 that accommodate a pair of electrical feedthroughs 76 (see FIG. 4). Each feedthrough includes a copper rod 78 surrounded by heat-shrinkable tubing insulation 80. Copper rod 78 is soldered to a brass cone 82 which is, in turn, seated upon a ceramic insulating cylinder 84. A stainless steel set screw 86 screws into the lower region of passageways 70 or 72 in pressure seal 16.

With respect to lower pressure seal 18 (FIG. 5), a high pressure, stainless steel gas tubing feeds into passageway 74, which in turn communicates with the interior of tube 14.

To perform a test, the upper boron nitride insert 30 is fastened to the heating element 20, which is then connected to the electrical vias 78 (feed-throughs) of the upper pressure seal 16. This assembly is then inserted in the interior of the tube 14. Prior to mounting the tube 14 in the test chamber 12, the ends of the tube 14 are wrapped with a 6" wide strip of aluminum foil (not shown). This foil serves to conduct the cooling effects of the water from the end caps 32 to the tube 14 and to more easily facilitate the removal of tube fragments from within the end caps 32 following fracture of the tube 14. The tube specimen is held up in the upper end cap 32 while the lower boron nitride insert 30 and pressure seal 18 are inserted in the interior of the tube 14. Water flow through cooling blocks (end caps) 32 is then commenced and power applied to heat the tube 14 to the desired test temperature. When the test temperature is reached, automatic controls enable steady gas pressurization of the tube 14 to a static pressure or to failure. Thus, both time-dependent and fast fracture strength behavior of tubes can be evaluated.

The pressure at which fracture occurs is indicated by one or more gauges attached to the gas pressure supply. Temperature measurements are taken via thermocouple(s) placed within tube 14 (e.g., via additional openings in upper pressure seal 16, see FIG. 3.

In FIG. 6 an arrangement is shown for testing a single ended tube. In this instance, pressure seal 16 also provides an orifice for pressurization, in addition to pathways for electrical connection to heater 20. There is no requirement for a lower pressure seal.

Cooled pressure seals 16 and 18 have a number of major advantages over hot end seals. First, ceramic-tube-metal bonding technology is not employed. Stress concentrations and/or chemical alterations of the tube specimen are avoided. Further, through the use of expandable O-rings, the tube under test remains unconstrained axially and is essentially free floating. Internal heating of the tube is advantageous in that only a single heating element is required. (If it were heated externally, a number of heating elements would be needed to distribute the heat around the circumference of the tube). Finally, by internally heating the tube, the fragments of the tube, upon failure can be captured by surrounding insulation and can be collected for examination. If an external furnace were used, both the furnace and the tube fragments would be damaged when the tube exploded.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. A testing apparatus for enabling a tubular member to be tested under pressure at an elevated temperature, the apparatus comprising:
a first pressure seal internal to a first end of said tubular member, and a second pressure seal internal to a second end of said tubular member, both said pressure seals including annular pliant members which bear upon the internal surface of said tubular member;
a heater positioned within said tubular member, a said pressure seal provided with an orifice through which said heater is connectable to a power source;
pressurizing means communicating with the interior of said tubular member via a said pressure seal for pressurizing said interior of said tube to a high pressure test level; and
cooling means surrounding said first and second ends of said tubular member for cooling said ends to enable said annular pliant members to retain their pliancy when said heater raises said tubular member to a test temperature.

2. Testing apparatus as recited in claim 1 wherein each said pressure seal comprises:
a shaft having an expanded portion;
an O-ring surrounding said shaft; and
a bushing surrounding said shaft, said O-ring sandwiched between said bushing and said expanded portion, said bushing dimensioned to exhibit a slip fit with respect to the internal surface of said tubular member, whereby pressurization of the interior of said tubular member compresses said bushing against said O-ring causing said O-ring to expand against the internal surface of said tubular member and both seal and support said tubular member.

3. The testing apparatus as recited in claim 2 wherein said orifice includes a conical shape, said heating apparatus further including electrical conductor means positioned within an insulating tubular member, said insulating tubular member including a conical external surface that mates with said conical shape of said orifice, whereby pressurization of said tubular member forces said conical surfaces together to create a seal.

4. The testing apparatus as recited in claim 2 wherein said cooling means comprises first and second metal members having orifices for receiving said first and second pressure seals, both said metal members provided with liquid cooling passageways.

5. The testing apparatus as recited in claim 4, further comprising a frame encompassing said metal members, said frame maintaining said metal members in place when said tubular member is pressurized 6. The testing apparatus of claim 5 wherein said pressurizing means pressurizes said tubular member and forces said pressure seals to bear against said metal members, said seals maintained in position by said metal members.

7. The testing apparatus as recited in claim 6 further comprising an enclosure for confining said tubular member when a fracture occurs.

8. The testing apparatus as recited in claim 2 wherein said heater exhibits an extended cylindrical shape and further comprising;
insulating cylinders positioned about said heating cylinder and adjacent said pressure seals to provide thermal insulation therefor.

9. A testing apparatus for enabling a tubular member to be tested under pressure at an elevated temperature said tubular member open at a first end and closed at a second end, the apparatus comprising:
a pressure seal internal to a first end of said tubular member and including an annular pliant member which bears upon the internal surface of said tubular member;
a heater positioned within said tubular member, said pressure seal provided with an orifice through which said heater is connectable to a power source;
pressurizing means communicating with the interior of said tubular member via said pressure seal for pressurizing said interior of said tube to a high pressure test level; and
cooling means surrounding at least said first end of said tubular member for cooling said end to enable said annular pliant member to retain its pliancy when said heater raises said tubular member to a test temperature.

10. Testing apparatus as recited in claim 9 wherein said pressure seal comprises:
a shaft having an expanded portion;
an O-ring surrounding said shaft; and
a bushing surrounding said shaft, said O-ring sandwiched between said bushing and said expanded portion, said bushing dimensioned to exhibit a slip fit with respect to the internal surface of said tubular member, whereby pressurization of the interior of said tubular member compresses said bushing against said O-ring causing said O-ring to expand against the internal surface of said tubular member and both seal and support said tubular member.

11. The testing apparatus as recited in claim 10 wherein said orifice in said pressure seal includes a conical shape, said heating apparatus further including electrical conductor means positioned within an insulating tubular member, said insulating tubular member including a conical external surface that mates with said conical shape of said orifice, whereby pressurization of said tubular member forces said conical surfaces together to create a seal.

* * * * *